US008268781B2

(12) United States Patent
Gotthardt et al.

(10) Patent No.: US 8,268,781 B2
(45) Date of Patent: Sep. 18, 2012

(54) PEPTIDE DERIVATIVES OF EXENDIN-4

(75) Inventors: Martin Gotthardt, Kirchhain (DE); Martin Béhé, Marburg (DE); Thomas Behr, Marburg (DE); Burkhard J. Göke, Gauting (DE)

(73) Assignee: Philipps-Universitat Marburg, Marburg (DE)

( * ) Notice: Subject to any disclaimer, the term of this patent is extended or adjusted under 35 U.S.C. 154(b) by 1364 days.

(21) Appl. No.: 11/712,978

(22) Filed: Mar. 2, 2007

(65) Prior Publication Data

US 2009/0180953 A1 Jul. 16, 2009

Related U.S. Application Data

(63) Continuation of application No. PCT/DE2005/001503, filed on Aug. 26, 2005.

(30) Foreign Application Priority Data

Sep. 3, 2004 (DE) .......................... 10 2004 043 153

(51) Int. Cl.
*C07K 14/575* (2006.01)

(52) U.S. Cl. ........ 514/11.7; 514/6.7; 514/7.2; 514/21.3; 530/308; 530/324; 424/1.69

(58) Field of Classification Search ........................ None
See application file for complete search history.

(56) References Cited

U.S. PATENT DOCUMENTS

| 2003/0036504 A1* | 2/2003 | Kolterman et al. | ............. 514/12 |
| 2003/0073626 A1 | 4/2003 | Hathaway et al. | |
| 2003/0232761 A1 | 12/2003 | Hinke et al. | |

FOREIGN PATENT DOCUMENTS

| DE | 690 18 226 | 9/1995 |
| WO | 91/01144 | 2/1991 |

OTHER PUBLICATIONS

File Scisearch on STN. An No. 2000:901410. Gotthardt et al. Scintigraphic detection of insulinomas by [I-123]glucagon-like peptide-1 and its analogue [I-123]-exendin4 [Y39] in a rat tumor model. Journal of Nuclear Medicine, (May 2000) vol. 41, No. 5, Supp. [S], pp. 9p-9P. (abstract only).*
Gibril et al. Somatostatin Receptor Scintigraphy: Its Sensitivity Compared with That of Other Imaging Methods in Detecting Primary and Metastatic Gastrinomas. Annals of Internal Medicine, vol. 125, No. 1 pp. 26-34. Jul. 1996.*
File Medline on STN. An No. 1996024164. Olsen et al. Somatostatin receptor imaging of neuroendocrine tumors with indium-111 pentetreotide (Octreoscan). Seminars in nuclear medicine, (Jul. 1995) vol. 25, No. 3, pp. 251-261. 1996 (abstract only).*
H. Stennicke et al., "C-Terminal Incorporation of Fluorogenic and Affinity Labels Using Wild-Type and Mutagenized Carboxypeptidase Y", *Analytical Biochemistry 248*, 141-148 (1997).
C. Montrose-Rafizadeh et al., "High Potency Antagonists of the Pancreatice Glucagon-like Peptide-1 Receptor", *The Journal of Biological Chemistry*, vol. 272, No. 34, Issue of Aug. 22, pp. 21201-21206, 1997.
L. Knudsen et al., "Potent Derivatives of Glucagon-like Peptide-1 with Pharmacokinetic Properties Suitable for Once Daily Administration", *J. Med. Chem.* 2000, 43, pp. 1664-1669.
Q. Xiao et al., "Biological Activities of Glucagon-Like Peptide-1 Analogues in Vitro and in Vivo", *Biochemistry 2001*, 40, pp. 2860-2869.
C. Deacon et al., "Dipeptidyl peptidase IV resistant analogues of glucagons-like peptide-1 which have extended metabolic stability and improved biological activity", *Diabetologia* (1998) 41: 271-278.
R. Göke et al., "Solubilization of active GLP-1 (7-36)amide receptors from RINm5F plasma membranes", *Federation of European Biochemical Societies*, vol. 300, No. 3, pp. 232-236, Apr. 1992.
J. Abello et al., "Stimulation of Glucagon-Like Peptide-1 Secretion by Muscarinic Agonist in a Murine Intestinal Endocrine Cell Line", *Endocrinology*, vol. 134, No. 5, 1994, pp. 2011-2017.
T. Behr et al., "Imaging tumors with peptide-based radioligands", *Q J Nucl Med 2001*; 45; pp. 189-200.

* cited by examiner

*Primary Examiner* — Anish Gupta
(74) *Attorney, Agent, or Firm* — Clark & Brody

(57) ABSTRACT

In the current invention peptides, which are derived from GLP-1 (glucagon-like peptide-1) and exendin-3 and/or exendin-4, are provided which bond to the GLP-receptor and can be used, labeled or unlabeled, for the production of an agent for diagnostic and therapy of benign and malignant diseases, in which GLP-1 receptor expression plays a role.

7 Claims, No Drawings

SEQUENCE LISTING

```
<160> NUMBER OF SEQ ID NOS: 3

<210> SEQ ID NO 1
<211> LENGTH: 37
<212> TYPE: PRT
<213> ORGANISM: Human
<220> FEATURE:
<221> NAME/KEY: GLP-1
<222> LOCATION: (1)..(37)
<300> PUBLICATION INFORMATION:
<302> TITLE: GLP-1 and Exendin related invention
<310> PATENT DOCUMENT NUMBER: DE 10 2004 043 153.1
<311> PATENT FILING DATE: 2004-09-03
<312> PUBLICATION DATE: 2006-09-03
<313> RELEVANT RESIDUES IN SEQ ID NO: (1)..(37)

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 39
<212> TYPE: PRT
<213> ORGANISM: human
<220> FEATURE:
```

```
<221> NAME/KEY: Exendin-3
<222> LOCATION: (1)..(39)
<300> PUBLICATION INFORMATION:
<302> TITLE: GLP-1 and Exendin related invention
<310> PATENT DOCUMENT NUMBER: DE 10 2004 043153.1
<311> PATENT FILING DATE: 2004-09-03
<312> PUBLICATION DATE: 2006-09-03
<313> RELEVANT RESIDUES IN SEQ ID NO: (1)..(39)

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: human
<220> FEATURE:
<221> NAME/KEY: Exendin-4
<222> LOCATION: (1)..(39)
<300> PUBLICATION INFORMATION:
<302> TITLE: GLP-1 and Exendin related invention
<310> PATENT DOCUMENT NUMBER: DE 102004043153.1
<311> PATENT FILING DATE: 2004-09-03
<312> PUBLICATION DATE: 2006-09-03
<313> RELEVANT RESIDUES IN SEQ ID NO: (1)..(39)

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

PEPTIDE DERIVATIVES OF EXENDIN-4

This application is a continuation of International Patent Application No. PCT/DE2005/001503, filed Aug. 26, 2005. This PCT application was not in English as published under PCT Article 21(2).

The invention at hand concerns a method for the production of a pharmacon for the depiction and therapy of primarily gastroenteropancreatic tumors, but also other benign and malignant diseases of different organ systems, based upon the incretin hormone GLP-1 and the analogs thereof.

DESCRIPTION AND INTRODUCTION OF THE GENERAL FIELD OF THE INVENTION

In the localization of gastroenteropancreatic neuroendocrine tumors, somatostatin receptor scintigraphy (SRS) is the most important diagnostic method next to ultrasound. The principle here is the specific depiction of tumors with the help of radioactively labeled peptides, which are absorbed by the tumor cells. Then, with the help of gamma cameras, the accumulation of the radioactivity in the tumor tissue can be verified visually. When a type of tumor possesses one of the necessary receptors for SRS, e.g. for the somatostatin analog Octreotide®, verification of these tumors is unproblematic. If corresponding receptors are not expressed, however, they evade scintigraphic verification. In addition to localization diagnosis, radioactive labeled peptides also allow for an approach to the treatment of tumors in which one can implement a specific receptor-directed radiopeptide therapy through labeling a somatostatin analog, e.g. Octreotide®, with an appropriate radionuclide ($\alpha$- or $\beta$-emitter). The fact that the corresponding radionuclides are bound chemically by the peptide (e.g. through complexation with a metal chelator which was previously bound to that peptide) in such a way that they will indeed be absorbed by the tumor cells but can no longer be discharged, results in a high specific accumulation in the tumor tissue.

However, a whole series of neuroendocrine tumors (NET), among them insulinomas and small cell bronchial carcinomas, do not express the necessary subtypes of the somatostatin receptor which are essential for SRS or radiopeptide therapy with the somatostatin analog Octreotide®. A substantial percentage of insulinomas in particular are not detectable by scintigraphic diagnosis. In small cell bronchial carcinomas SRS also does not constitute an appropriate method as, although primary tumors are often visible, metastases are not able to be shown due to loss of receptor expression. Consequently they are inaccessible for radiopeptide therapy, which presents an interesting additional or alternative therapy method. Therefore the need exists for an appropriate peptide, which will be absorbed by the previously mentioned tumors.

The incretin hormone glucagon-like peptide-1 (GLP-1), as well as its analogs exendin-3 and exendin-4 (from the saliva of the gila monster *Heloderma horridum* and *Heloderma suspectum*), are peptides, for which insulinomas and small cell bronchial carcinomas—along with many other kinds of tumors—express receptors. Insulinomas originate from the insulin producing $\beta$-cells in the islet of Langerhans in the pancreas, in which GLP-1 as well as exendin-3 and exendin-4 elicit a postprandial insulin secretion.

TECHNICAL STATE OF THE ART

For the utilization of glucagon-like peptide-1 (GLP-1) in scintigraphy it is necessary to label the peptide. The method for that and for the labeling of proteins with radionuclides is known to the expert and documented in numerous patent applications (e.g. DE 690 18 226 T2) and scientific publications. The peptides described there for application in diagnostic imaging and for the exchange of therapeutically effective molecules in pathological tissue are normally inserted on the N-terminal end through an amino in the peptide. The peptides must be further modified concurrently regarding stabilization.

The GLP-1 used in the US 2003/0232761A1 and its derivative GLP-1(7-37) are, for example, modified on the N-terminal end by one amino. Hence, the N-terminal end of GLP-1 is no longer available to bond a GLP-1 receptor, therefore both receptor bonding and internalization is inadequate in these peptides. The latter are thus inappropriate for utilization in radiopeptide therapy of insulinomas and small cell bronchial carcinomas. As experience shows, a mutation, such as a substitution of an amino acid within the sequence of peptides of GLP-1 and exendin 3 or exendin 4, and their possible modifications through a therapeutic or a signalizing molecule most often causes damage to the peptide structure, obstructing any further bonding to the receptor.

A further method for the modification of GLP-1, without affecting the N-terminus, is not known at this time. Furthermore, no GLP-1 derivatives are known which are appropriate, either labeled or unlabeled, for use in the radiotherapy of insulinomas and small cell bronchial carcinomas.

TASK

The task of the invention at hand, therefore, is to eliminate the deficiency of the technological state of the art and make peptides available which can be labeled and still bond the GLP-1 receptor with this labeling and be utilized in the production of an agent for the diagnosis and therapy of diseases, in which the expression of the GLP-1 receptor plays a role.

SOLUTION OF THE TASK

This task is solved, based on the present invention, by the claims, through peptide derivatives of GLP-1, exendin-3 and exendin-4, which are modified by an amino at the C-terminus and bond via the N-terminus at the GLP-1 receptor as well as chimeric peptides of GLP-1 with exendin-3 or exendin-4. These peptide derivatives as well as the chimeric peptides are being unlabeled or labeled in order to be utilized in the production of an agent for diagnostic and therapy of benign or malignant diseases in which GLP-1 receptor expression plays a role.

Through these peptide derivatives of GLP-1, exendin-3 and exendin-4 as well as chimeric peptides of GLP-1, exendin-3 or exendin-4 the production of a means for scintigraphic applications is carried out which will be utilized for diagnostic and therapy of GLP-1 receptor expressing tumors, including NET (especially from insulinomas) and small cell bronchial carcinomas.

This is possible for the first time, as the peptide derivatives based on the current invention are modified by an amino at the C-terminus, making thus available the N-terminus for bonding to the GLP-1 receptor.

Through the bonding of the peptide derivatives based on the current invention, for instance radioactively labeled, and chimeric peptides of GLP-1, exendin-3 and exendin-4 to the GLP-1 receptor, the representation of GLP-1 receptor expressing tumors is possible, enabling hereby a considerable improvement of the patients' medical care. NET are, above all, gastroenteropancreatic NET, such as insulinomas, for which to date no non-invasive method with sufficient sensitivity is available or of small cell bronchial carcinomas localized in the area of the lung in which case the specific differentiation between inflammable processes and tumors or metastases is neither possible by means of a non-invasive method.

Furthermore, by means of the peptide derivatives and the chimeric peptides, both based in the current invention, the density of insulin producing cells within the pancreas as well as the expression of GLP-1 receptors in vivo and in vitro are visualized. This is for instance in the representation of GLP-1 receptor expressing cells in the case of the diabetes mellitus a in vivo representation, as these are the cells which also secrete insulin. The representation of the GLP-1 receptor density within the pancreas is particularly important in the case of patients with diabetes mellitus during and after therapy with pharmaceuticals.

Additionally the distribution of GLP-1 receptors in malignant and benign tissues is represented. The articulated questions are hereby both of clinical as well as of scientific nature, as there is to date no all inclusive data available concerning the arrangement of GLP-1 receptors in human beings.

Thus, the advantage of the current invention is that peptide derivatives of GLP-1 (glucagon-like peptide-1), exendin-3 and exendin-4 as well as chimeric peptides of GLP-1, exendin-3 or exendin-4 are utilized for the production of an agent, especially for the receptor-oriented specific representation and therapy, particularly of NET, in the case at hand especially of insulinomas and small cell bronchial carcinomas.

A GLP-1 receptor scintigraphy is particularly applicable in the diagnosis of small cell bronchial carcinomas, allowing for the first time the specific detection of metastases within lymph nodes (lymph nodes changed by inflammation versus lymph nodes attacked by metastases).

The application of peptide derivatives from (glucagon-like peptide-1), exendin-3 und exendin-4, as well as chimeric peptide from GLP-1, exendin-3 or exendin-4 according to the current invention remains an agent of diagnostic and therapy for all malignant and benign diseases in which GLP-1 receptor expression plays a role, in particular in the following: as a contrast agent in Magnetic Resonance Imaging (MRI); as a radioactive agent in scintigraphy (SPECT, Single Photon Emission Computed Tomography) as well as in radiopeptide therapy; in PET (Positron Emissions Tomography); in receptor-mediated chemotherapy; and in optical diagnostic. Optical diagnostic here means the stimulation of a fluorescent molecule by a particular wave length, inducing a successive light emission of a different wave length. It is the emitted wave length which is detected.

An expert can easily choose the kind of labeling at the C-terminus of the peptide derivative from GLP-1 (glucagon-like peptide-1), exendin-3 and exendin-4 as well as the chimeric peptides from GLP-1, exendin-3 or exendin-4 depending on the desired application: for example, for scintigraphy or radiotherapy from radioactive nuclides; for contrast agent in Magnetic Resonance Imaging (MRI) from gadolinium; and for endoscopic or scientific examinations from fluorescent pigments.

According to the current invention malignant diseases are those in which the affected tissue shows changes in its level of differentiation as compared to healthy tissue, invasive growth or a spreading of its tissue into the blood stream or lymphatic system. All neuroendocrine tumors fall into this category, in particular those of the gastrointestinal tract; especially insulinomas, bronchial carcinomas, pancreatic carcinomas and all other malignant diseases which are connected to the overexpression of GLP-1 receptors.

According to the current invention benign diseases are those characterized by the fact the affected tissue does not significantly lose its level of differentiation, shows no invasive growth and does not have any tissue metastasis into the blood stream or lymphatic system. This includes, for example, diabetes mellitus, but also eating disorders of disorders of the psyche.

Characterization of Peptide Derivatives and Chimeric Peptides

Surprisingly it was found that peptide derivatives from GLP-1, exendin-3 and exendin-4, as well as chimeric peptides from GLP-1, exendin-3 or exendin-4, which are modified via an amino at the C-terminus, bond at the N-terminus to the GLP-1 receptor. They even shown a high degree of affinity to the GLP-1 receptor, as do natural peptides. Experiments with tumor carrying hairless mice show a specific uptake in GLP-1 receptors of positive tumor tissue.

Peptide derivatives as well as chimeric peptides according to the current invention are unlabelled or, via a chelator at the C-terminus amino, labeled as an agent for application in the diagnostic and therapy of benign and malignant diseases in which GLP-1 receptor expression plays a role. The type of labeling here consists mainly of a radiometal, a MRI contrast agent, a fluorescent chromophore or a chemotherapeutic agent.

The process and method of labeling are well known to an expert (e.g. DE 690 18 226 T2), which take place, for example, through the coupling of radionuclides, non-magnetic metals and other MRI contrast agents or fluorescent pigments; this means that the bonding of the receptors or the internalization of the peptide derivatives, as well as the chimeric peptides according to the current invention, are not impaired and the GLP-1 receptor bonding N-terminus remains free (unlinked).

The sequences of amino acids of the original peptides:

```
GLP-1:
H-His-Asp-Glu-Phe-Glu-Arg-His-Ala-Glu-Gly-Thr-
  1   2   3   4   5   6   7   8   9   10  11

Phe-Thr-Ser-Asp-Val-Ser-Ser-Tyr-Leu-Glu-Gly-Gln-
12  13  14  15  16  17  18  19  20  21  22  23

Ala-Ala-Lys-Glu-Phe-Ile-Ala-Trp-Leu-Val-Lys-Gly-
24  25  26  27  28  29  30  31  32  33  34  35

Arg-Gly-OH
36  37

Exendin-3:
H-His-Ser-Asp-Gly-Thr-Phe-Thr-Ser-Asp-Leu-Ser-
  1   2   3   4   5   6   7   8   9   10  11

Lys-Gln-Met-Glu-Glu-Glu-Ala-Val-Arg-Leu-Phe-Ile-
12  13  14  15  16  17  18  19  20  21  22  23

Glu-Trp-Leu-Lys-Asn-Gly-Gly-Pro-Ser-Ser-Gly-Ala-
24  25  26  27  28  29  30  31  32  33  34  35

Pro-Pro-Pro-Ser-NH₂
36  37  38  39

Exendin-4:
H-His-Gly-Glu-Gly-Thr-Phe-Thr-Ser-Asp-Leu-Ser-
  1   2   3   4   5   6   7   8   9   10  11

Lys-Gln-Met-Glu-Glu-Glu-Ala-Val-Arg-Leu-Phe-Ile-
12  13  14  15  16  17  18  19  20  21  22  23

Glu-Trp-Leu-Lys-Asn-Gly-Gly-Pro-Ser-Ser-Gly-Ala-
24  25  26  27  28  29  30  31  32  33  34  35

Pro-Pro-Pro-Ser-NH₂
36  37  38  39
```

According to the current invention the following peptide derivatives of GLP-1 (1-37), exendin-3 and exendin-4 are produced:

GLP-1(x-y)A$^{1-37}$
Exendin-3 (z-k)A$^{1-40}$
Exendin-4 (z-k)A$^{1-40}$

Whereby:
x=amino acids 1-36 of the GLP-1 amino acid sequence
y=amino acids 2-37 of the GLP-1 amino acid sequence
z=amino acids 1-38 of the exendin-3 or exendin-4 amino acid sequence
k=amino acids 2-39 of the exendin-3 or exendin-4 amino acid sequence
A=Attachment group consisting of one or more amino acid or its derivative as a signal molecule, or to bond signal molecules or to stabilize them. The preference is for A to be located at the C-terminus and the amino is preferably lysine or alternatively another amino acid with a free amino, e.g. ornithine or an organic group with a free amino onto which a chelator is coupled for the labeling with radionuclides or a MRI contrast agent, fluorescent pigments or a chemotherapeutic agent.

Chelators which can be used include DTPA (diethylenetriaminepentaacetic acid), alternatively N,N-Bis(2-[bis(carboxymethyl)amino]-ethyl)glycine), alternatively DOTA (1,4,7,10-tetraazacyclododecane-1,4,7,10-tetra-acetic acid), HYNIC (6-hydrazinopyridin-3-carbonic acid), MAG3 (mercaptoacetyl-glycylglycylglycine), N4 (1,4,8,11-tetraazaundecane) and all known derivatives of the above named chelators.

The exponent indicates at which position the attachment group alternatively can be found within the amino acid sequence.

GLP-1(x-y)A$^{1-37}$

Here GLP-1 derivatives of different lengths are included, whereby x can accept the numbers 1 to 36, which is smaller than y, which accepts the numbers 2 to 37. A is the attachment group which can be placed at any position, preferably however at the C-terminus and is one higher than y. Preferably, the attachment group is the amino lysine.

Exendin-3 (z-k)A$^{1-40}$

Here exendin-3 derivatives of different lengths are included, whereby z can accept the numbers 1 to 38, which is smaller than k, which accepts the numbers 2 to 39. A is the attachment group which can be placed at any position, preferably, however, at the C-terminus and is one higher than y. Preferably, the attachment group is the amino lysine.

Exendin-4 (z-k)A$^{1-40}$

Here exendin-4 derivatives of different lengths are included, whereby z can accept the numbers 1 to 38, which is smaller than k, which accepts the numbers 2 to 39. A is the attachment group which can be placed at any position, preferably, however, at the C-terminus and is one higher than y. Preferably, the attachment group is the amino lysine.

The following peptide derivatives are particularly preferred:
1. MC 10: (DTPA-Lys$^{37}$) GLP1 (7-36) amide
2. MC 13: (DTPA-Lys$^{40}$) exendin-3 amide
3. MC 11: (DTPA-Lys$^{40}$) exendin-4 amide The synthesis takes place, for example, in the company Peptide Specialty Laboratories GmbH according to the Merrifield method and purification via HPLC.

MC 10 (DTPA-Lys$^{37}$) GLP1 (7-36) amide consists of the amino acids 7-36 of GLP-1, carrying at the C-terminal end as an amino acid with a free amino, preferably lysine at position 37 as well as the chelator DTPA.

MC 13 (DTPA-Lys$^{40}$) exendin-3 amide consists of the complete amino acid sequence of exendin-3, carrying at the C-terminal end as an amino acid with a free amino, preferably lysine at position 40 as well as the chelator DTPA.

MC 11 (DTPA-Lys$^{40}$) exendin-4 amide consists of the complete amino acid sequence of exendin-3, carrying at the C-terminal end as an amino acid with a free amino, preferably lysine at position 39 as well as the chelator DTPA.

According to the current invention the following chimeric peptides from GLP-1 (1-37) and exendin-3 or exendin-4 are produced:

GLP-1(x-y) exendin-3(z-k)A$^{1-75}$
GLP-1(x-y) exendin-4(z-k)A$^{1-75}$
Exendin-3(z-k) GLP-1(x-y)A$^{1-75}$
Exendin-4(z-k) GLP-1(x-y)A$^{1-75}$ Here the Following Applies:
x=amino acids 1-36 of the GLP-1 amino acid sequence
y=amino acids 2-37 of the GLP-1 amino acid sequence
z=amino acids 1-38 of exendin-3 or exendin-4 amino acid sequence
k=amino acids 2-39 of exendin-3 or exendin-4 amino acid sequence
A=Attachment group consisting of one or more amino acid or its derivative as a signal molecule, or to bond signal molecules or to stabilize them. The preference is for A to be located at the C-terminus and the amino is preferably lysine or alternatively another amino acid with a free amino, e.g. ornithine or an organic group with a free amino onto which a chelator is coupled for the labeling with radionuclides or a MRI contrast agent, fluorescent pigments or a chemotherapeutic agent.

Chelators which can be used include DTPA (diethylenetriaminepentaacetic acid), alternatively N,N-Bis(2-[bis(carboxymethyl)amino]-ethyl)glycine), alternatively DOTA (1,4,7,10-tetraazacyclododecane-1,4,7,10-tetra-acetic acid), HYNIC (6-hydrazinopyridin-3-carbonic acid), MAG3 (mercaptoacetyl-glycylglycylglycine), N4 (1,4,8,11-tetraazaundecane) and all known derivatives of the above named chelators.

The exponent indicates at which position the attachment group alternatively can be found within the amino acid sequence.

GLP-1(x-y) exendin-3(z-k)A$^{1-75}$

Here chimeric peptides from GLP-1 and exendin-3 are included, in which the amino acids 1 to 36 come from GLP-1 and then after that the amino acids 1 to 39 from exendin-3. A is the attachment group which can be placed at any position, preferably, however, at the C-terminus, and is one higher than the number of amino acids from GLP-1 and exendin-3, preferably the amino lysine.

GLP-1(x-y) exendin-4(z-k)A$^{1-75}$

Here chimeric peptides from GLP-1 and exendin-3 are included, in which the amino acids 1 to 36 come from GLP-1 and then after that the amino acids 1 to 39 from exendin-4. A is the attachment group which can be placed at any position, preferably, however, at the C-terminus, and is one higher than the number of amino acids from GLP-1 and exendin-4, preferably the amino lysine.

Exendin-3(z-k) GLP-1(x-y)A$^{1-75}$

Here chimeric peptides from exendin-3 and GLP-1 are included, whereby z can accept the numbers 1 to 38, but is smaller than k, which can accept the numbers 2 to 39. A is the attachment group which can be placed at any position, preferably, however, at C-terminus and is one higher than y. Preferably, the attachment group is the amino lysine.

Exendin-4(z-k) GLP-1(x-y)A$^{1-75}$

Here chimeric peptides from exendin-4 and GLP-1 are included, whereby z can accept the numbers 1 to 38, but is smaller than k, which can accept the numbers 2 to 39. A is the attachment group which can be placed at any position, preferably, however, at C-terminus and is one higher than y. Preferably, the attachment group is the amino lysine.

Exemplary for a chimeric GLP-1(x-y) exendin-3(z-k)$A^{1-75}$ or GLP-1(x-y) exendin-4(z-k)$A^{1-75}$ peptide is MC12, consisting of GLP-1 (7-36) exendin (33-39) Lys amide (Synthesis takes place in the company Peptide Specialty Laboratories GmbH according to the Merrifield method and purification via HPLC.).

MC 12: ($Ser^{37}$, $Gly^{38}$, $Ala^{39}$, $Pro^{40}$, $Pro^{41}$, $Pro^{42}$, $Ser^{43}$, DTPA-$Lys^{44}$ amide) GLP1 (7-36)

MC 12 consists of the complete amino acid sequence of GLP-1 (7-36), carrying at the C-terminal end an amino, preferably lysine at position 44 as well as the chelator DTPA, as well as a chain of 7 amino acids from exendin (33-39) Lys amide. Thus there is a chimeric peptide GLP-1 (7-36) exendin (33-39)Lys amide.

It is clear to the expert that hereby peptide derivatives of different lengths from GLP-1, exendin-3 and exendin-4, as well as chimeric peptides of different lengths from GLP-1, exendin-3 or exendin-4 exist, which contain various combinations of the amino acid sequences from GLP-1, exendin-3 and exendin-4 on which they are based.

The peptide derivatives from GLP-1, exendin-3 and exendin-4, as well as chimeric peptides from GLP-1, exendin-3 or exendin-4 based on the current invention, which are modified by an amino at the C-terminus and bond via the N-terminus at the GLP-1 receptor, also include molecules which are distinguishable at one or more positions from the peptide GLP-1, exendin-3 and exendin-4 described above and have a high degree of homology to those sequences. Homology here means a sequence identity of at least 40%, in particular an identity of 60%, preferably over 80% and especially preferably over 90%. The deviation to the amino acid sequences described above could arise through deletion, substitution and/or insertion Furthermore, the chimeric peptides from GLP-1, exendin-3 or exendin-4 according to the current invention are also produced without any modifications to the C-terminus. They are particularly used in the production of an agent for the therapy of diabetes.

GLP-1(x-y) exendin-3(z-k)
GLP-1(x-y) exendin-4(z-k)
Exendin-3(z-k) GLP-1(x-y)
Exendin-4(z-k) GLP-1(x-y)

MC 20: ($Ser^{33}$, $Gly^{34}$, $Ala^{35}$, $Pro^{31}$, $Pro^{37}$, $Pro^{38}$, $Ser^{39}$) exendin GLP1 (7-36)

MC 20 consists of the complete amino acid sequence of GLP-1 (7-36), carrying at the C-terminal end a chain of 7 amino acids from exendin (33-39). Thus there is an unmodified chimeric peptide GLP-1 (7-36) exendin (33-39).

Labeling of the Peptide Derivatives and the Chimeric Peptides

Peptide derivatives as well as chimeric peptides according to the current invention are dissolved in a suitable stabilizing buffer, for example, in order to stabilize metals, preferably in 0.5 M sodium acetate pH 5.4 with a concentration of approx. $10^{-3}$ M. Alternatively, for the stabilization of fluorescent pigments a buffer of ammonium acetate is preferable; for the stabilization of chemotherapeutic agent and contrast agents a physiological buffer is preferable.

The labeling occurs at the attachment group A through the coupling of radionuclides, MRI contrast agents, fluorescent pigments or chemotherapeutic agent. Different methods are applied according to whether the application will be in vitro or in vivo.

The following are used as Radionuclides for Covalent or Complex Coupling:

| Nuclide | Procedure in which applied | $t_{1/2}$ [h] | Emitted radiation | Energy [keV] | Type of coupling |
|---|---|---|---|---|---|
| F-18 | PET | 1.8 | $\beta^+$ | 634 | covalent |
| Cu-64 | PET | 12.7 | $\beta^+$ | 1673 | complex |
| Cu-67 | therapy | 61.8 | $\beta^-$ | 391 | complex |
| | | | $\gamma$ | 184 | |
| Ga-67 | SPECT | 79.2 | $\gamma$ | 93/184/300 | complex |
| Ga-68 | PET | 1.1 | $\beta^+$ | 2921 | complex |
| Y-86 | PET | 14.8 | $\beta^+$ | 1220 | complex |
| | | | $\gamma$ | 1076/1153 | |
| Y-90 | therapy | 64.1 | $\beta^-$ | 2280 | complex |
| Tc-99m | SPECT | 6 | $\gamma$ | 140 | complex |
| In-111 | SPECT | 67.2 | $\gamma$ | 171/245 | complex |
| I-123 | SPECT | 13.2 | $\gamma$ | 158 | covalent |
| I-124 | PET | 101 | $\beta^+$ | 2137/1534 | covalent |
| | | | $\gamma$ | 602 | |
| I-131 | therapy | 192 | $\gamma$ | 364 | covalent |
| | | | $\beta^-$ | 606 | |
| Lu-177 | therapy | 158 | $\gamma$ | 208 | complex |
| | | | $\beta^-$ | 112/208 | |
| Re-186 | therapy | 88.8 | $\gamma$ | 137 | complex |
| | | | $\beta^-$ | 1071 | |
| Re-188 | therapy | 17 | $\gamma$ | 155/477/632 | complex |
| | | | $\beta^-$ | 1965/2120 | |
| Pt-193m | therapy | 104 | $\gamma$ | 135 | complex |
| | | | auger $e^-$ | | |
| Pt-195m | therapy | 96 | $\gamma$ | 98 | complex |
| | | | auger $e^-$ | | |
| Ac-225 | therapy | 240 | $\gamma$ | 99,150 | complex |
| | | | $\alpha$ | | |
| At-211 | therapy | 7.2 | $\gamma$ | 687 | complex |
| | | | auger $e^-$ | | covalent |
| Bi-213 | therapy | 0.76 | $\gamma$ | 440 | complex |
| | | | $\alpha$ | | |
| Sm-153 | therapy | 46 | $\gamma$ | 103 | complex |
| | | | $\beta^-$ | | |
| Er-169 | therapy | 226 | $\beta^-$ | 100 | complex |

PET (Positron Emissions Tomography), SPECT (Single Photon Emissions Computed Tomography)

Fluorescent pigments/chromophores such as the following were used: Fluorescein, Rhodamin, Coumarin, BODIPY, Pyrene (Cascade Blue), Lucifer Yellow, Phycobiliprotein, Cyanin, AlexaFluoro, Oregon Green, Texas Red and their derivatives.

Chelators which can be used include DTPA (diethylenetriaminepentaacetic acid), alternatively N,N-Bis(2-[bis(carboxymethyl)amino]-ethyl)glycine), alternatively DOTA (1,4,7,10-tetraazacyclododecane-1,4,7,10-tetra-acetic acid), HYNIC (6-hydrazinopyridin-3-carbonic acid), MAG3 (mercaptoacetyl-glycylglycylglycine), N4 (1,4,8,11-tetraazaundecane) and all known derivatives of the above named chelators.

MRI contrast agents which can be used include: gadolinium, manganese, iron, europium, copper, nickel, chrome, prasodymium, dysprosium or holmium or their compounds, but also the negative MRI contrast agents such as perfluorocarbone, as well as isotopes such as such as F-19, H-1, P-31, Na-19 for MRI spectroscopy. Negative MRI contrast agents according to the current invention are those which obliterate the MRI signal or greatly weaken it, i.e. not amplifying it.

Chemotherapeutic agents which can be used include: alkylating agents, intercalators, antimetabolite, enzyme inhibitors and blockers and spindle poisons (for example alkylsulfonate, ethylimine, nitrosomonas (*N. ureae*), nitrogen mustard derivatives, folic acid analogs, purine analogs, pyrimidine analogs, podophyllin derivatives, taxane, vincaalcaloide, anthracycline, other cytostatic antibiotics, platinum compounds, campthotecin derivatives, different hormones, growth factors, interferons or interleukins), otherwise the chemotherapeutic agents described in "Onkologie 2004/05", authors Preiss, Dornhoff, Hagmann, Schmieder, published by Zuckschwerdtverlag, at pp. 230-287, but also all other cytostatic or cytotoxic substances.

Depending on the type of application in which the protein derivatives and chimeric proteins according to the current invention are used, and the agent produced with the above mentioned proteins for diagnostic and therapy of benign and malignant diseases, in which GLP-1 receptor expression plays a role, the labeling reaction will be carried out in two variations.

Labeling for In Vitro Application in Radiotherapy

3 µL of the peptide derivative or the chimeric peptide according to the invention which has been dissolved in a suitable stabilizing buffer, preferably 0.5 M sodium acetate pH 5.4 with a concentration of approx. $10^{-3}$ M, are added to 500 µL 0.5 M sodium acetate pH 5.4 for the purpose of labeling. The pH-value is between 3 and 6. Then 185 MBq $^{111}InCl_3$ (Tyco, Petten, The Netherlands) in 0.1 M HCl 500 µL is added and incubated for 30 minutes at 37° C. Finally 3 µL $10^{-3}$ M solution $^{nat}InCl_3$ is added, followed by a further incubation for 30 min in order to saturate all bond sites.

Quality control is carried out via a HPLC column:
Column: CC 250/4.6 Nucleosil 120-5 C18 (Machery-Nagel, Oenisingen, Switzerland)
Gradient: 0->5 min 100% 0.05 M $NH_4OOCCH_3$, pH 5.4 (buffer A); 5->25 min 100% buffer A->50% buffer A/50% acetone nitrile.
Quality control for an in vitro application is fulfilled with a labeling yield of over 98

Thus a radioactive labeled agent is available for diagnostic and therapy of benign and malignant diseases, in which GLP-1 receptor expression plays a role, which can, for example, which can be employed in cell and tissue cultures of pancreatic cells.

Labeling for In Vivo Application in Radiotherapy

3 µL of the peptide derivative or the chimeric peptide according to the invention which has been dissolved in a suitable stabilizing buffer, preferably 0.5 M sodium acetate pH 5.4 with a concentration of approx. $10^{-3}$ M, are added to 500 µL 0.5 M sodium acetate pH 5.4 for the purpose of labeling. Finally 185 MBq $^{111}InCl_3$ (Tyco, Petten, The Netherlands) in 0.1 M HCl 500 µL is added and incubated for 30 minutes at 37° C. Quality control is carried out via a HPLC-Column:
Column: CC 250/4.6 Nucleosil 120-5 C18 (Machery-Nagel, Oenisingen, Switzerland)
Gradient: 0->5 min 100% 0.05 M $NH_4OOCCH_3$, pH 5.4 (buffer A); 5->25 min 100% buffer A->50% buffer A/50% acetone nitrile.
Quality control for an in vivo application is fulfilled with a labeling yield of over 98

Thus a radioactive labeled agent is available for diagnostic and therapy of benign and malignant diseases, in which GLP-1 receptor expression plays a role, which can, for example, be employed to detect tumors in patients.

The term "patient" refers to humans and vertebrates alike. Thus, the agent can be applied both in human and veterinary medicine. The therapeutically and diagnostically effective agent based on the current invention is given to patients as part of an acceptable pharmaceutical composition in one of the following forms: oral, rectal, parenteral, intravenous/intraarterial, intramuscular, subcutaneous, intrathecal, intracisternal, intracranial, intravaginal, intraperitoneal, intravascular, local (powder, ointment or drops) or spray form (aerosol).

The required dose is to be determined by a doctor in each individual case of diagnostic and therapy of benign and malignant diseases, in which GLP-1 receptor expression plays a role.

Internalization Study

The internalization study shows, in exemplary manner, the transport into the cell of the peptide derivatives and chimeric proteins, both in vitro radioactively labeled, according to the current invention.

In a 6 well plate 100,000 GLP-1 receptor transfected CHO cells are sown. The cells grow until they are confluent. Then 4 groups are formed:

Group 1: Complete Bonding, Washed with PBS 100,000 cpm $^{111}$In ($10^{-15}$ Mol) labeled peptide is added to 2 mL medium and incubated for 1 h at 37° C. Then it is washed 3× with PBS and the cells are separated with 20 mM MOPS (3-Morpholinopropanesulfonic-acid)+0.1% Triton-X-100 (ph7.4). The uptake into the cells is measured with a γ-counter. The number of cells is measured by the protein content, using the protein assay kit from Bio-Rad (Munich, Germany), based on the Bradford method. The results are given in proteins cpm/µg.

Group 2: Non-Specific Bonding, Washed with PBS

20 µL of a $10^{-3}$ M GLP-1 solution and 100,000 cpm $^{111}$In labeled peptide are added to 2 mL medium and incubated for 1 h at 37° C. Then it is washed 3× with PBS and the cells are separated with 20 mM MOPS (3-Morpholinopropanesulfonic-acid)+0.1% Triton-X-100 (ph7.4). The uptake into the cells is measured with a γ-counter. The number of cells is measured by the protein content, using the protein assay kit from Bio-Rad (Munich, Germany), based on the Bradford method. The results are given in proteins cpm/µg.

Group 3: Complete Bonding, Washed with Acid

20 µL of a $10^{-3}$ M GLP-1 solution and 100,000 cpm $^{111}$In labeled peptide are added to 2 mL medium and incubated for 1 h at 37° C. Then it is washed 1× with 0.1 M sodium acetate buffer pH 4 and 2× with PBS and the cells are separated with 20 mM MOPS (3-Morpholinopropanesulfonic-acid)+0.1% Triton-X-100 (ph7.4). The uptake into the cells is measured with a γ-counter. The number of cells is measured by the protein content, using the protein assay kit from Bio-Rad (Munich, Germany), based on the Bradford method. The results are given in proteins cpm/µg.

Group 4: non-specific bonding, washed with acid

20 µL of a $10^{-3}$ M GLP-1 solution and 100,000 cpm $^{111}$In labeled peptide are added to 2 mL medium and incubated for 1 h at 37° C. Then it is washed 1× with 0.1 M sodium acetate buffer pH 4 and 2× with PBS and the cells are separated with 20 mM MOPS (3-Morpholinopropanesulfonic-acid)+0.1% Triton-X-100 (ph7.4). The uptake into the cells is measured with a γ-counter. The number of cells is measured by the protein content, using the protein assay kit from Bio-Rad (Munich, Germany), based on the Bradford method. The results are given in proteins cpm/µg.

$$\text{Evaluation: } \% \ IDsB = \frac{\text{Res}3. - \text{Res}4.}{\text{Res}1. - \text{Res}2.} * 100$$

% IdsB = % of internalization of the specific bonding

|  | % IdsB |
| --- | --- |
| MC10 | 75 ± 5 |
| MC11 | 70 ± 7 |
| MC12 | 73 ± 9 |

The results show that a good transport has taken place into the cells.

Bonding Studies

Bonding studies show the specific bonding which takes place via the vivo-labeling radioactive labeled peptide derivatives and chimeric proteins according to the current invention onto the GLP-1 receptor.

In a 6-well plate 100,000 GLP-1 receptor transfected CHO cells are sown. The cells grow until they are confluent. Then 2 mL 100,000 cpm $^{111}$In labeled peptide is added. In order to test the bonding it is then blocked with 20 μL of a $10^{-3}$ M GLP-1 solution.

|  | % Blocking |
| --- | --- |
| MC10 | 80 ± 3 |
| MC11 | 85 ± 3 |
| MC12 | 77 ± 6 |

The in vivo bio-distribution can, for example, be shown in rodents such as hairless mice. For this purpose GLP-1 transfected CHO cells are injected into hairless mice. After approx. 3 to 5 weeks tumors approx. 300 mg in size had grown. The mice are then injected in a tail vein with 37 MBq $^{111}$In labeled peptide according to the invention and are measured after 4 h under a γ-camera.

In the course of this procedure there was quick clearance via the kidneys and an uptake in the kidneys. There was also a high uptake in the GLP-1 receptor positive tumor, whereas the GLP-1 receptor negative tumor barely showed any uptake. There was also a slight uptake in the pancreas; other organs showed no visible uptake.

Ex vivo bio-distribution studies are conducted in groups of 4 mice each, in which 555 kBq In-111 labeled MC10 is injected into the tail vein. 1, 4 und 24 h p.i. all the mice are killed and their organs removed.

The uptake of radioactivity is measured and the organs are weighed. The % of injected dose program of organ weight is calculated.

The results are as follows:

| Organ | 1 h | Stadev | 4 h | Stadev | 24 h | Stadev |
| --- | --- | --- | --- | --- | --- | --- |
| Blood | 0.01 | 0.00 | 0.00 | 0.00 | 0.00 | 0.00 |
| Liver | 0.03 | 0.01 | 0.01 | 0.01 | 0.01 | 0.00 |
| Stomach | 0.14 | 0.10 | 0.13 | 0.07 | 0.07 | 0.06 |
| Spleen | 0.02 | 0.02 | 0.01 | 0.00 | 0.01 | 0.00 |
| Pancreas | 0.58 | 0.50 | 0.62 | 0.28 | 0.37 | 0.27 |
| Kidneys | 7.90 | 3.62 | 7.41 | 3.56 | 4.85 | 3.05 |
| Intestine | 0.12 | 0.06 | 0.07 | 0.06 | 0.04 | 0.03 |
| Lungs | 0.80 | 0.56 | 0.36 | 0.17 | 0.22 | 0.07 |
| Heart | 0.02 | 0.01 | 0.01 | 0.01 | 0.00 | 0.00 |
| Bones | 0.02 | 0.04 | 0.01 | 0.00 | 0.01 | 0.01 |
| Muscle | 0.01 | 0.00 | 0.00 | 0.00 | 0.00 | 0.00 |
| Tumor− | 0.03 | 0.03 | 0.02 | 0.01 | 0.01 | 0.00 |
| Tumor+ | 0.42 | 0.19 | 0.31 | 0.30 | 0.20 | 0.16 |

Mean value from the bio-distribution with 4 mice pro group in % i.D./g Stadev: standard deviation.

The invention claimed is:

1. Peptide derivatives of exendin-4, wherein their C-terminus is modified by an amine and wherein their N-terminus binds to the GLP-1 receptor, of the formula exendin-4 (1-39)-A, wherein exendin 4 (1-39) corresponds to a sequence identity of over 90% to the amino acid sequence of

```
                                              (SEQ ID NO 3)
H-His-Gly-Glu-Gly-Thr-Phe-Thr-Ser-Asp-Leu-Ser-Lys-
   1   2   3   4   5   6   7   8   9  10  11  12

Gln-Met-Glu-Glu-Glu-Ala-Val-Arg-Leu-Phe-Ile-Glu-
 13  14  15  16  17  18  19  20  21  22  23  24

Trp-Leu-Lys-Asn-Gly-Gly-Pro-Ser-Ser-Gly-Ala-Pro-
 25  26  27  28  29  30  31  32  33  34  35  36

Pro-Pro-Ser-NH₂;
 37  38  39
``` with A being an attachment group, which is located at the C-terminus and represents a lysine, and wherein a chelator is coupled with the attachment group A for the labeling with radionuclides.

2. Peptide derivatives from exendin-4 according to the claim 1, wherein the chelator is N,N-Bis(2-[bis(carboxymethyl)amino]-ethyl)glycine), DOTA (1,4,7,10-Tetraazacyclodo-decane-1,4,7,10-tetra-acetic acid), HYNIC (6-Hydrazinopyridin-3-carbonic acid), MAG3 (mercaptoacetyl-glycylglycylglycine), N4 (1,4,8,11-tetraazaundecane).

3. Peptide derivatives from exendin-4 according to the claim 1, wherein the chosen radionuclide is in particular from the group F-18, Cu-64, Cu-67, Ga-67, Ga-68, Y-86, Y-90, Tc-99m, In-111, I-123, I-124, I-131, Lu-177, Re-186, Re-188, Pt-193m, Pt-195m, Ac-225, At-211, Bi-213, Sm-153 or Er-169.

4. Agent for the diagnostic and therapy of benign and malignant diseases, in which GLP-1 receptor expression plays a role, wherein it contains labeled peptide derivatives of exendin-4 according to claim 1.

5. Agent according to claim 4 wherein the labeled peptide derivatives contain a radionuclide.

6. Agent according to the claim 5, wherein after labeling with radionuclides for in vitro applications, free bonding sites are saturated with $^{nat}InCL_3$.

7. Peptide derivatives from extendin-4 according to claim 2, wherein the chelator is DTPA (Diethylenetriaminepentaacetic acid).

* * * * *